(12) United States Patent
Chen

(10) Patent No.: US 6,225,471 B1
(45) Date of Patent: *May 1, 2001

(54) PREPARATION OF PYRAZINES

(75) Inventor: Teh-Kuei Chen, Gaylordsville, CT (US)

(73) Assignee: Nestec S.A., Vevey (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 07/851,810

(22) Filed: Mar. 16, 1992

Related U.S. Application Data

(63) Continuation-in-part of application No. 07/675,417, filed on Mar. 26, 1991, now abandoned.

(51) Int. Cl.[7] .................................................. C07D 241/12
(52) U.S. Cl. .............................................................. 544/410
(58) Field of Search ............................................. 544/410

(56) References Cited

U.S. PATENT DOCUMENTS

| | | | |
|---|---|---|---|
| 3,067,199 | * 12/1962 | Langdon | 544/410 |
| 3,676,442 | * 7/1972 | Bonzom | 544/410 |
| 4,064,124 | * 12/1977 | Weitz et al. | 544/410 |
| 4,855,431 | * 8/1989 | Chang et al. | 544/410 |

FOREIGN PATENT DOCUMENTS

97983 * 8/1977 (JP).

OTHER PUBLICATIONS

Akiyama et al, *J. Agric. Food Chem.* 26, p1176 (1978).*
"Techniques of Organic Chemisty" (Arnold Weissberger, Ed.), vol. IV, pp613–618, 627, 628 (1951).*
Evans et al, *Aust. J. Chem.*, 25, p2671 (1972).*
Bell et al, *Aust. J. Chem.* 32, p1281 (1979).*
Rizzi, *J. Agric. Food Chem.* 36, p349–352 (1988).*

* cited by examiner

*Primary Examiner*—Richard L. Raymond
(74) *Attorney, Agent, or Firm*—Vogt & O'Donnell, LLP

(57) ABSTRACT

Alkyl pyrazine compounds are prepared by heating and refluxing an aqueous mixture of an ammonium-containing compound and at least one acyloin compound. Reaction product may be isolated from the reacted mixture by adjusting the pH of the reacted mixture, separating solid material from the pH-adjusted reacted mixture, adding water to the separated solid material to form a solution, allowing product to crystallyze from the solution and then collecting the crystalline product. Alternatively, the reactants may be heated, refluxed and sublimed to collect the pyrazine reaction product on a cooled sublimation collection surface.

18 Claims, 1 Drawing Sheet

PREPARATION OF PYRAZINES

CROSS REFERENCE TO RELATED APPLICATION

Figure 1:
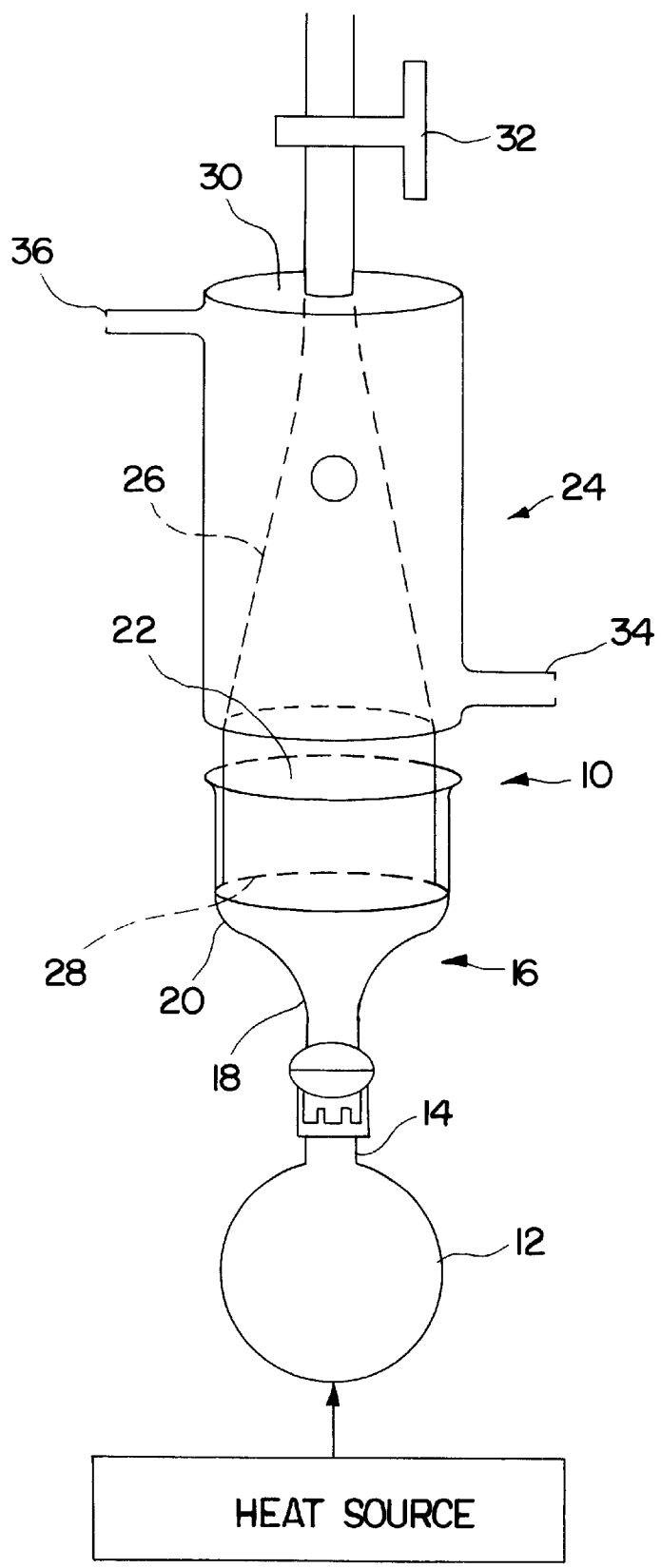

This is a continuation-in-part application of Application Ser. No. 07/675,417, filed Mar, 26, 1991, now abandoned.

BACKGROUND OF THE INVENTION

The present invention relates to preparation of pyrazine compounds and/or compositions containing the same.

Pyrazine compositions and derivatives thereof are known to have utility in varieties of applications in various industries as broad-ranging as the pharmaceutical, dyestuff and rubber industries. A plurality of reactant compounds and compositions and reaction mechanisms and conditions have been described, proposed and suggested in the art, including such as those described in U.S. Pat. No. 3,067,199, wherein alkanolamine compounds are disclosed to be reacted with nickel or cobalt hydrogenation/dehydrogenation catalysts at elevated temperature which is said to "favor" pyrazine formation when carried out under sub-atmospheric pressure; in U.S. Pat. No. 3,676,442, wherein acetylene compounds are reacted with an ammoniacal derivative under acid conditions at elevated pressure; in U.S. Pat. No. 4,855,431, wherein pyrazines are prepared by passing an aminoalkyl over a particular crystalline aluminosilicate zeolite composition; and in Japanese Kokai 52-97983, wherein an acyloin compound and an ammonium salt of an acid are heated, as exemplified, with a heat-stable solvent, under neutral or acidic conditions.

As indicated by G. P. Rizzi, in J. Arig. Food Chem. Vol. 36 No. 2, 1988, pp. 349–352, who proceeded to study the nature of pyrazine formation from acyloin compounds and ammonium compounds by reactions which included reflux conditions, although alkyl pyrazines have been widely investigated as trace components in foods, their exact origin remains a mystery.

Rizzi notes that alkyl pyrazines have been found in fermented products, and it also is believed that pyrazine compounds tend to be formed during cooking, roasting, or baking of various foodstuffs and thus have importance as flavor components of such foodstuffs. In particular, it is believed that these compounds impart roast flavor and aromatic characteristics to foodstuffs and also may impart charred notes which are desirable in moderation. Thus, efforts are being made to attempt to prepare such compositions in a food-acceptable manner.

As will be noted from the above-noted art, however, procedures to isolate pyrazine compounds from a reaction mixture are generally complex and, but for one embodiment of U.S. Pat. No. 3,676,442, wherein a filtering and crystallyzation of the desired product is disclosed, that art teaches complex solvent extraction and/or distillation isolation steps.

SUMMARY OF THE INVENTION

The present invention provides processes for the preparation and isolation of alkyl pyrazines, particularly tetraalkyl pyrazines, and is characterized in that an aqueous medium containing ammonium ions, such as provideed by an ammonium-containing compound, and at least one acyloin compound having the general formula:

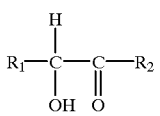

wherein $R_1$ and $R_2$ are the same or different and are alkyl group of prepared, and the aqueous medium is having from 1 to 3 carbon atoms, are heated and refluxed to obtain a reacted mixture, and an alkylpyrazine compound is isolated from the reacted mixture.

Most advantageously, the reaction is carried out under a pressure less than atmospheric pressure, which has been discovered to increase the yield of the product.

The isolation of the reaction product prepared by heating and refluxing is characterized in that a base is added to the reaction mixture to adjust the pH of the liquid of reacted mixture to an alkaline pH, solid material is separated from the pH-adjusted liquid of the reacted mixture, water is added to dissolve the solid material to form a solution, and the product then is allowed to crystallyze from the solution after which, the crystalline product is recovered from the liquid phase by separating it from the liquid phase. Thus, the isolation, which is particularly useful when $R_1$ and $R_2$ of the acyloin are both methyl, avoids inter alia the need for time consuming steps of organic extraction and/or distillation steps known in the arts The present invention is further particularly characterized in that, in a most advantageous embodiment, an alkylpyrazine reaction product is prepared and isolated from a reacted mixture of an acyloin and an ammonium-containing compound by a simultaneous combination of heating, refluxing and sublimation for collection of the product on a cooled sublimation collection surface.

The products of the present invention provide desirable flavorants which may be added to a variety of foodstuffs to impart at least overall non-species-specific roasted notes. Products of the present invention, therefore, are combined advantageously in food compositions.

DETAILED DESCRIPTION OF THE INVENTION

In the practice of the present inventions, although ammonia gas could be bubbled through an acyloin, with or without water, to provide ammonium ions to effect the reaction, it is most practical to employ an aqueous solution of an ammonium-containing compound including the ammonium salts of organic and inorganic acids, and other equivalent ammonium-containing compounds to provide ammonium ions in the aqueous medium. Employment of ammonium salts of weak acids is preferred since it has been found that such act as a buffer agent against formation of acetic acid and hence, buffer the pH, which decreases during the reaction. Such ammonium salts include ammonium acetate, citrate, formate, lactate, oxalate, succinate and tartrate, and diammonium phosphate, etc., individually or in combination.

Other ammonium salts of stronger acids, while not being particularly effective as buffers, also may be employed to effect the reaction, and such include ammonium chloride and sulfate, etc., and when the pyrazine product is to be employed with a food composition, all such ammonium-containing compounds should of course be deemed to be acceptable in processes related to preparing food products.

The acyloin compositions and the ammonium salts are advantageously employed in a molar ratio of about 1:1 to about 1:3, and preferably, about 1:1.5 to about 1:3, acyloin: ammonium salt, and above. Although it also has been found that the higher the amount of ammonium salt, the better the buffering action and the greater the rate of reaction, amounts of ammonium salt higher than the 1:3 ratio, noted above, have not been found to increase yield significantly, and also have been found to generate less than desirable amounts of ammonia gas. Thus, other basic buffering agents are employed usefully to maintain the reaction mixture weakly acidic, and such has been found to reduce generation of ammonia gas. Such agents may include compounds such as sodium acetate, trisodium phosphate and other alkali salts and the like. Again, if the final product is to be employed in a food application, such agents should be deemed acceptable for use in processes related to preparing food products.

In general, the pH of the reaction mixture will not fall below a pH of about 4.5 to 5 and the buffering agents may be employed to maintain a pH of above 5.

Although the amount of water employed may vary considerably, generally, as the amount of water is increased, the reaction rate decreases. Thus, although the amount of water present may range from about 0.5 to about 100 parts by weight per part of the total weight of acyloin and ammonium salt employed, the amount most advantageously employed is merely that amount sufficient to place the ammonium-containing composition, and any pH-adjusting compositions, in solution at the reaction temperatures.

A dehydrogenating, or aromatization, agent which accepts hydrogen advantageously is employed to increase the reaction rate and yield. Such agents may be employed in an amount of about 1 molar ratio, preferably in a molar ratio from about 0.50 to about 0.70, based on the molar amount of acyloin. Hydrogen peroxide is preferred. However, other dehydrogenation agents, particularly other peroxides, such as peroxyacetic acid, peroxybenzoic acid and m-chloroperoxybenzoic may be employed. In addition, other dehydrogenating agents may include selenium, sulfur and organic disulfides, and the like, for example. In general, what are known to the artisan as mild dehydrogenating agents are preferred, and of course, when the pyrazine product is to be employed in food applications, the dehydrogenating agent should be deemed to be acceptable for preparing food products.

In the practice of the present inventions wherein the reactants are heated and refluxed only, any suitable heat-stable vessel, as is known in the reflux art, may be employed. Of course, if the reaction is carried out in excess of atmospheric pressure or under reduced pressure, the reaction vessel should also be pressure stable.

As will be appreciated, heating temperatures on the order of about 100° C. generally are required to obtain reflux conditions, and in general, increasing the reaction temperature increases the rate of the reaction. Temperatures on the order of up to about 200° C., or even above, may be employed, and temperatures on the order of from about 110° C. to about 150° C. are preferred.

The time of reaction employed is not critical, other than to the extent such impacts upon yield, and such may range up to about 15 hours, but it has been found that good yields may be obtained with reaction times on the order of even less than one hour, and generally with reaction times of from about 2 hours to 8 hours.

As indicated above, most advantageously, heating and refluxing are carried out under a reduced pressure which also has been discovered to increase the yield of the pyrazine product. Thus, a refluxing system may be evacuated with a vacuum-generating means such as a vacuum pump, and then closed from the vacuum-generating means prior to heating and reacting the mixture. Reduced pressures on the order of from about 5 mm Hg to about 150 mm Hg may be employed, and reduced pressures on the order of from about 20 mm Hg to about 50 mm Hg are preferred.

In the reflux embodiment discussed above, the reaction product is contained in the reacted mixture. Isolation of the desired product is effected by increasing the pH of the liquid reacted mixture to an alkaline pH, i.e., above pH of about 7, after which solid material is separated from the pH-increased liquid by means such as filtering or centrifuging, for example. Preferably, the pH is increased to at least about 8, which may be performed under ambient conditions.

Bases which may be employed to increase the pH of the liquid of the reacted mixture are preferably strong bases and include NaOH, KOH and $NH_4OH$, and the like. Such are preferably added in aqueous solution since it is desirable to dilute the reacted mixture with water. Generally, a dilution of up to 3 parts water to 1 part reacted mixture is desired. Thus, depending upon the strength and concentration of the base, water also may be added before or after addition of the base to dilute the reacted mixture.

As indicated above, water is employed to dissolve the solid material obtained from the pH-adjusted reacted mixture. Hence, water in an amount and at a temperature sufficient to dissolve the solid material product is added to the solid material product. The temperature of the water added to the solid product may range, for example, from temperatures of from about 50° C. to about 100° C., and as will be appreciated, the higher the temperature, the more quickly the solid material will dissolve and, in general, the less the amount of water required. Generally, water in an amount to provide a water to solid product ratio of from 5:1 to 10:1 by weight may be employed. The solution then is allowed to cool, and a crystalline product thus forms which may be recovered from the liquid phase by filtering or centrifuging, or other appropriate means.

In the reflux/sublimation embodiment, although one may perform such at atmospheric pressure, reduced pressures on the order of from about 5 mm Hg to about 100 mm Hg are preferred since reduced pressures provide, in particular, for an enhanced sublimation rate and improved isolable yield. Reduced pressures on the order of from about 20 mm Hg to 50 mm Hg preferably are employed. The temperatures employed for reflux may be those set forth above.

For sublimation, the collecting surface generally should be cooled to a temperature of below at least about 20° C., such as which cooling water, and temperatures provided by refrigerant materials, i.e., freons and liquified gases, etc., known to the art, to enable the condensing surface to cool to the freezing point of a desired product also may be employed, such being particularly useful for isolation of ethyl- and propyl-pyrazine compounds and mixtures thereof, although such could be collected as liquids with sublimation means which are known in the art.

In the reflux/sublimation embodiment, the only caveats for the apparatus system employed are that such be capable of the dual function of refluxing and sublimation. Thus, the criteria for such a system is that it enable heating the reactants and that it have a cooled surface for enabling collection of the product. Thus, a variety of sublimation configurations, as are known in the art and as may be constructed readily by the artisan, may be employed. If the cooled surface of the system is not readily detachable from the system, as will be appreciated, cooling of the collection surface should be continued until the reaction medium and remainder of the system has cooled. Of course, in a continuous system, product may be removed at least periodically while quantities of the reactants are reacting which will assist in efficiency of isolation and collection.

Thus, in the reflux/sublimation embodiment, a crystalline product forms on the sublimation collection surface, and after physical removal of the product from the sublimation surface by any of various means known to one in the art, such as by a scraping means, the product then may be washed with chilled water at a temperature which will not dissolve the product. The product and washing water may and then be filtered and the product obtained is dried, or the product may be otherwise separated from the washing water and dried, washing water may be employed also to remove product from the sublimation collection surface.

BRIEF DESCRIPTION OF THE DRAWING FIGURE

The accompanying drawing FIGURE illustrates a reflux/sublimation assembly employed in certain of the Examples set forth below.

DETAILED DESCRIPTION OF THE DRAWING FIGURE

The drawing FIGURE illustrates an assembly, generally designated by reference numeral 10, which enables one to carry out reflux heating and sublimation simultaneously. In the assembly, round bottom flask 12 has a narrow neck 14 to which is connected narrow-neck connecting reducing adapter 16. Adapter 16 flares out from its neck 18 to a body portion 20 to an open end 22. Sublimation body 24, known in the art as an ACE GLASS sublimation device, is fitted over open adapter end 22 and contains a sublimation cooling collection body surface 26, which is in a form of a cone, the wide end 28, of which, fits fluid-tight in adapter body portion 20.

For drawing a vacuum, end 30 of sublimation cooling collection body surface cone 26 is provided with an opening. Means, such as are known to those skilled in vacuum sublimation the art, including such as stop-cock 32, etc., are provided for sealing off cone 26 from the vacuum source.

In operation, the desired reactants are placed in flask 12 which then is fitted to adapter 16 and connected to sublimation body 24. The reactants in the flask are heated by appropriate means to the reflux temperatures noted above, which thereby drives reaction product up through adapter 16 into cooling collection cone 26. Cooling fluid is transported about cone 26 in sublimation body 24 by means of the inlet and outlets 34 and 36.

Thus, by reason of the arrangement of the elements of assembly 10, cooled liquid drops back into the flask. As this is occurring, however, reaction product sublimes as crystals on the collection body cone 26 which, after termination of refluxing, cooling such as to room temperature to enable ease of handling, adjustment to atmospheric pressure, and disassembly of the system, is removed as noted above.

As also will be appreciated, in a configuration such as above, there may be a tendency for the desired product to fall downwards towards the reaction flask. Hence, a narrow-neck reaction flask is preferred in such a configuration, and it may be found that further product will collect in the adapter body. In addition, any product in the reaction mixture may be isolated by the procedures noted above and also described in certain Examples below.

EXAMPLES

The following Examples further illustrate the present invention. Parts and percentages are by weight unless otherwise indicated. Melting points (uncorrected) are determined by employing an ELECTROTHERMAL melting point apparatus.

EXAMPLE 1

Acetoin (10.6 g, 0.12 moles), 27.8 g ammonium acetate (0.36 moles) and 2.5 ml of water are placed in a 100 ml round bottom flask. The flask is open to the atmosphere, and the mixture is heated to a temperature of about 110° C. and refluxed for about 7 hours during which time a reddish-colored reacted mixture formed. The flask and reacted mixture are cooled to enable handling.

To isolate the pyrazine compound from the reacted mixture, the reacted mixture is diluted with 70 ml of water, and a solution of 20% NaOH is added to the diluted reacted mixture to adjust it to a pH of 10. The pH-adjusted reacted mixture is filtered to remove solid material. Hot water is added to the solid material to dissolve the solid material, and the solution is allowed to cool, during which time crystalline needles form in the aqueous medium. The aqueous medium is filtered from the crystals, and 4.7 g of the crystalline needles are collected. The crystalline material is found to have a melting point range of from 83° C. to 85° C. Analyses indicate that the product is tetramethylpyrazine. The calculated yield is 57.4%.

EXAMPLE 2

The same reactants and amounts of reactants employed in Example 1 are mixed in a flask connected to a vacuum pump. The flask is evacuated to a reduced pressure of 30 mm Hg, closed off from the vacuum source, and then heated to about 110° C. and refluxed for about 6.5 hours during which time an orange-colored reacted mixture is formed. The pyrazine composition is isolated by the procedures of Example 1 and provides 5 g of crystallized product. Analyses indicate that the product obtained is tetramethylpyrazine. The product has a melting point of from 83° C. to 85° C. The calculated yield is 61%.

EXAMPLE 3

Acetoin (3.52 g 0.04 moles), diammonium phosphate (6 g 0.045 moles) in 5 ml of water are heated in a flask immersed in an oil bath which is maintained at a temperature of 125° C. for 6 hours. The pyrazine product is isolated by following the procedures of Example 1. 1.4 g of a crystalline product is obtained. Analyses indicate that the product is tetramethylpyrazine. The product has a melting point of from 84° C. to 85° C. The calculated yield is 55.5%.

EXAMPLE 4

Acetoin (10.6 g, 0.12 moles), ammonium acetate (25 g, of 0.29 moles) and 8 ml of 30% $H_2O_2$ (0.07 moles) and 25 ml of water are placed in a flask which is immersed in an oil bath heated to 125° C. and kept in the heated bath for 40 minutes. The reaction product is isolated by following the procedure of Example 1. 7.3 g of crystalline product is obtained. Analyses indicate that the product is tetramethylpyrazine. The product has a melting point of 84° C. to 85.5° C. The calculated yield is 89%.

EXAMPLE 5

Example 4 is repeated except that no $H_2O_2$ is added to the reactants. 4.3 g of product is obtained. Analyses indicate that the product is tetramethylpyrazine. The product has a melting point of from 84° C. to 86° C. The calculated yield is 52.4%.

EXAMPLE 6

Example 5 is repeated, except that the reactants are heated for 80 minutes. 5.1 g of crystalline product is obtained. Analyses indicate that the product is tetramethylpyrazine. The product has a melting point of from 84° C. to 86° C. The calculated yield is 62.2%.

EXAMPLE 7

Acetoin (7.92 g, 0.09 moles), ammonium acetate (21 g, 0.27 moles), and 2 ml of water are processed in an assembly as depicted in the drawing Figure. The assembly is evacuated to a reduced pressure of about 30 mm Hg. The reaction mixture is heated at 115° C. and refluxed for 4 hours. Crystalline product sublimed on the cooled cone. After cooling the system and releasing pressure, and after disassembly, the product is collected and washed with water. 3.7 g of a crystalline product are obtained. Analyses indicate the product is tetramethylpyrazine. The product has a melting point of from 83° C. to 85° C.

The remaining reacted mixture is diluted with 90 ml of 5% NaOH solution and then filtered. The collected solid is crystallized from hot water and filtered. 0.2 g of crystalline product is obtained. Analyses indicate the product is tetramethylpyrazine. The product has a melting point of from 84° C. to 86° C.

The total amount of product obtained provides a calculated yield of 63.7%.

EXAMPLE 6

A 150 ml WHITNEY T-valve stainless steel cylinder with a pressure gauge is loaded with 10.6 g of acetoin (0.12 moles), 22 g of ammonium acetate (0.24 moles) and 4 ml of water. It is evacuated to a reduced pressure of 20 mm Hg. The vessel then is heated in an oil bath at 125° C. for 6 hours. After cooling, 70 ml of hot water is added to the reaction product, and the contents of the cylinder are transferred to a beaker and the pH is adjusted to about 10. The pH-adjusted liquid is filtered, collected and crystallized from hot water. 5.2 g of crystalline product having a melting point of from 83° C. to 85° C. is obtained (yield 63.5%, m.p. 83–85° C.).

EXAMPLE 9

Example 8 is repeated except that no reduction in pressure is effected. 4.89 g of crystalline product having a melting point of from 83° C. to 85° C. is obtained. The calculated yield is 58.6%.

EXAMPLE 10

Acetoin (5.3 g), ammonium acetate (6 g), sodium acetate (9 g), 30% of $H_2O_2$ (4 g) in 4 ml of water are reacted in the assembly employed in Example 7 for 10 minutes at 60° C. and then for 3 hours at 125° C. following the procedure of Example 7. 3.75 g of sublimed crystalline product having a melting point of from 83° C. to 86° C. is collected from the assembly. The calculated yield is 91.5%.

EXAMPLE 11

Acetoin (5.3 g), ammonium acetate (6 g), sodium acetate (5 g), trisodium phosphate (4 g), and hydrogen peroxide 30% (4 g) in 7 ml of water are reacted under a vacuum as in Example 2 for 6 hours at a temperature of 105° C. 3.4 g of crystalline product is obtained (yield 82.9%, m.p. 83–85° C.).

EXAMPLE 12

Example 11 is repeated except that the refluxing is carried out at atmospheric pressure. 3.25 g of crystalline product is obtained (yield 79.3% m.p. 83° C. to 85° C.).

As is clear from the foregoing, various modifications of the present invention may be without departure from the spirit and scope of the disclosure, and the invention may be practiced suitably in the absence of elements not specifically disclosed herein.

I claim:

1. A process for preparation of alkyl-pyrazine compounds comprising steps of (a) preparing an aqueous medium containing ammonium ions and at least one acyloin compound having the general formula:

$$R_1-\underset{\underset{OH}{|}}{\overset{\overset{H}{|}}{C}}-\underset{\overset{\|}{O}}{C}-R_2$$

wherein $R_1$ and $R_2$ are the same or different and are alkyl groups having from 1 to 3 carbon atoms and of (b) simultaneously, heating, refluxing and subliming the aqueous medium and cooling a surface for collecting a sublimation product and collecting a sublimed alkyl-pyrazine product on the cooled surface.

2. A process according to claim 1 wherein the aqueous medium is heated, refluxed and sublimed at a pressure less than atmospheric pressure.

3. A process according to claim 2 wherein the pressure is from 5 mm Hg to 150 mm Hg.

4. A process according to claim 1 or 2 wherein $R_1$ and $R_2$ are methyl.

5. A process according to claim 1 or 2 wherein the cooled surface has a temperature of less than about 20° C.

6. A process according to claim 1 or 2 wherein the aqueous medium is prepared with an ammonium salt of an acid for providing the ammonium ions.

7. A process according to claim 1 or 2 wherein the aqueous medium is prepared further with a dehydrogenating agent.

8. A process according to claim 7 wherein the dehydrogenating agent is a peroxide.

9. A process according to claim 1 further comprising a step of removing collected sublimed product from the surface for isolating the product.

10. A process according to claim 9 further comprising a step of washing the isolated product with water.

11. A process according to claim 1 wherein the process steps consist essentially of the preparing, heating, refluxing, subliming, cooling and collecting steps.

12. A process according to claim 9 wherein the process steps consist essentially of the preparing, heating, reflexing, subliming, cooling, collecting and isolating steps.

13. A process for obtaining an alkyl-pyrazine compound consisting essentially of preparing an aqueous medium containing ammonium ions, a dehydrogenating agent and an acyloin compound having the formula:

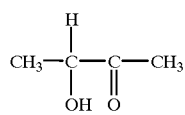

and heading and refluxing the aqueous medium to obtain a reaction medium, adding a base to the reaction medium to adjust the pH of the reaction medium to an alkaline pH, seperating reaction medium solid material from liquid material, adding water to the separated solid material to dissolve the solid material to obtain a solution, allowing a product to crystallize from the solution to obtain a solid product and a liquid phase and then seperating the solid product from the liquid phase to obtain the solid product.

14. A process according to claim 13 wherein the aqueous medium is heated and refluxed at a pressure less than atmospheric pressure.

15. A process according to claim 14 wherein the pressure is from 5 mm Hg to 150 mm Hg.

16. A process according to claim 13 or 14 wherein the pH of the liquid of the reaction medium is adjusted to a pH of at least about 8.

17. A process according to claim 13 or 14 wherein the aqueous medium is prepared further with an ammonium salt of an acid for providing the ammonium ions.

18. A process according to claim 13 or 14 wherein the dehydrogenating agent is a peroxide.

* * * * *

UNITED STATES PATENT AND TRADEMARK OFFICE
CERTIFICATE OF CORRECTION

PATENT NO.    : 6,225,471 B1
DATED         : May 1, 2001
INVENTOR(S)   : Teh-Kuei Chen Page 1 of 1

It is certified that error appears in the above-identified patent and that said Letters Patent is hereby corrected as shown below:

Column 2,
Lines 9-10, delete "group of prepared, and the aqueous medium is having from 1 to 3 carbon atoms, are" and insert therefor -- groups having from 1 to 3 carbon atoms, is prepared, and the aqueous medium is --.
Line 28, change "arts" to -- art. --.

Column 5,
Line 14, delete "and".
Line 16, after the comma after "dried", insert -- and --.

Column 9,
Line 8, (first text line under the claim 13 formula), change "heading" to -- heating --.

Signed and Sealed this

Eleventh Day of September, 2001

Attest:

*Nicholas P. Godici*

NICHOLAS P. GODICI
*Attesting Officer*   *Acting Director of the United States Patent and Trademark Office*